US006160893A

United States Patent [19]

Saunders et al.

[11] Patent Number: 6,160,893

[45] Date of Patent: Dec. 12, 2000

[54] FIRST DRAFT-SWITCHING CONTROLLER FOR PERSONAL ANR SYSTEM

[76] Inventors: William Richard Saunders, 2509 Plymouth St., Blacksburg, Va. 24060; Michael Allen Vaudrey, 208 Northlake Rd., Columbia, S.C. 29223

[21] Appl. No.: 09/123,974

[22] Filed: Jul. 29, 1998

[51] Int. Cl.[7] ...................................................... A61F 11/06

[52] U.S. Cl. ............................................................ 381/71.6

[58] Field of Search .............................. 381/71, 71.6, 68, 381/98, 71.1, 71.8, 72, 74, 312, 317, 318, 58, 56, 57, 60, 71.7, 93, 71.11, 71.12

[56] References Cited

U.S. PATENT DOCUMENTS

| | | | |
|---|---|---|---|
| 3,571,529 | 3/1971 | Gharib et al. ............................. | 381/68 |
| 5,481,615 | 1/1996 | Eatwell et al. ............................ | 381/71 |

*Primary Examiner*—Vivian Chang
*Attorney, Agent, or Firm*—James W. Hiney

[57] ABSTRACT

An active noise control system for use in testing hearing using a pure tone audiometry testing procedure and employing multiple switching controllers with pre-filtering means and a switch to select any one controller to provide a predetermined one and having the ability to configure each switching controller so that the maximum threshold shift occurs for the frequency of the test tone and for modifying each test tone in accordance with a standard calibration frequency.

31 Claims, 5 Drawing Sheets

FIRST DRAFT-SWITCHING CONTROLLER FOR PERSONAL ANR SYSTEM

SUMMARY

This invention relates to a unique control approach that provides a means for manual or automated switching of narrowband controllers in personal active noise reduction (ANR) systems. A second related innovation links the human auditory system's physiological features to the design of a specific switching controller that implements ANR technology in audiometric testing. For a given control objective of narrowband acoustic disturbance rejection, an analog or digital feedback controller can be designed to accomplish this goal over the precise bandwidth of the disturbance(s). This is accomplished primarily by designing a feedback controller with a resonant peak spanning the disturbance bandwidth and acceptable open loop phase and gain margins at higher frequencies. The bandwidth-to-performance ratio of a single controller is limited for this control approach, leading to performance degradation when the disturbance spectral content spans a broad bandwidth or is temporally changing. The new switching controller which comprises the subject matter of this invention requires that multiple feedback controllers be integrated with the personal ANR system, each one designed for maximum suppression/ minimum spillover over specific and different narrowbands of frequencies. In the presence of time-varying disturbances or control objectives, the switching controller will select the optimal configuration using user-selectable or automated switching to reduce those acoustic disturbance frequencies that dominate either the perceived noise suppression or the electronic performance in a specified bandwidth.

FIELD OF THE INVENTION

This invention relates to the idea of switching between many pre-designed feedback controllers with different design objectives for the same personal ANR system (e.g. ANR headset, ANR audiometer, etc.). The switching is accomplished by allowing the user to select the controller that is most useful for the immediate control goal; or by an automated system with a given set of criteria for incorporating one of many control approaches. This invention is most applicable to pure tone audiometry testing where single tones of varying frequencies are presented to the test subject at different times. By controlling specially-shaped, narrow bands of ambient noise immediately surrounding different test tones, the minimum hearing threshold can be more accurately determined. Because these shapes are physiologically motivated, and depend on the test tone frequency, the ANR controller's frequency response requirements will change as the test tone frequencies change. Existing realizations for personal ANR systems have been limited to only one single-in-single-out controller design. One fixed-gain controller cannot provide equal, or optimal, performance over the entire range of test tones because of an inability to change the controller's frequency response to mimic the auditory system's different masking patterns for the different test tone frequencies. The switching controller concept remedies this limitation through the provision of a set of separate controllers that can be designed for more effective reduction of broadband ambient masking noises by switching component controllers depending on the frequency of the audiometer test tone. Although the concept of switching narrowband controllers for ambient noise disturbance rejection is well-suited for audiometry testing, this invention is not so limited. This invention significantly enhances the effectiveness of personal ANR systems by providing all users with the ability to maximize their individually perceived noise suppression in any environment that exhibits changing spectral content or ambient noise spanning a wide bandwidth.

BACKGROUND OF THE INVENTION

This invention originated from research performed on the feasibility of using ANR technology to improve the performance of audiology testing. Hearing tests are conducted using "pure tone audiometers" that are designed to deliver a single frequency test-tone to the test subject at varying level. The proctor varies the sound pressure level of the tone and interrogates the subject about the lowest level that is audible. That level is the hearing threshold level of the test subject for that frequency. It is intuitive that the background noise in the test chamber can interfere with this threshold measurement. When the background noise levels are higher than the test tone level (at the ear) the test tone can be "masked" and it will appear to the user that his/her threshold is higher than it would be in a quieter environment. This masking effect is relatively narrowband in nature, due to the physiology of the ear. Therefore, it is not required to suppress ALL the background noise in order to alleviate the tonal masking. It is required that the frequencies of the background noise that are "nearby" the test tone be suppressed. Therefore, it became clear that it is not only desirable to place the frequency of maximum ANR suppression at the test tone frequency, it is actually essential that the controller provide its maximum suppression in the frequency bandwidth(s) surrounding the test tone(s). Therefore, a switching controller was built and tested. It works as expected. During this project, it became apparent that all personal ANR systems could benefit from this type of ANR architecture.

In audiometry testing, it is desirable to occlude any ambient noise in the testenvironment in order to accurately identify the subject's minimum hearing threshold. Pure tone audiometry testing uses a unique set of single tones, standard for all pure tone audiometers, to identify this minimum threshold. As the tone varies, so must the controller design. Previously, the background noise masking has been reduced (or nearly eliminated) by using sound proof booths (called test booths) or by using a product known as ear inserts, or by a passive earcup (audiocup) installed over the hearing test equipment. The ANR technology performs as well, perhaps better, than some of these products. There are no ANR audiometers in the market place.The bode integral theorem limits the amount of control that can be realized across a wide range of frequencies for a single, fixed-gain controller (i.e. the classic ANR headset). This means that it would be beneficial to circumnavigate this problem by providing a master system with the ability to "call up" different feedback controllers that do not try to extend performance over a very broad bandwidth.

There are two distinct aspects to this invention. One is that no existing personal ANR systems rely on a switching controller. The other is that prior to this invention audiometers have never used ANR, The background prior art does not show any use of a personal ANR system (i.e. ANR headset, ANR communications headset, silent seat, etc.) that utilizes a series of controllers that can be switched by the user or some automation algorithm/hardware. The instant approach is clearly desirable if one does not have accurate knowledge of the acoustic noise that must be suppressed for the user. For example, the BOSE headset uses a fixed-gain controller with the maximum noise suppression occurring at approximately 200 Hz, and tapering off to no suppression with decreasing and increasing frequency. If the disturbance noise did not contain frequencies between 100 Hz and 300 Hz the BOSE controller wouldn't be very useful in suppressing noise. This switching controller invention relies on multiple fixed-gain controllers, designed as an entity called a switching controller. The user, or a method, can then switch to the particular fixed-gain controller design that performs best for the noise field impinging upon the user. This should lead to the best reduction of background noise, using either electronic measurements or psychoacoustic perception metrics such as loudness.

Having described the invention in general terms, the objects of the invention are related below.

OBJECTS OF THE INVENTION

Accordingly, it is an initial object of this invention to apply feedback active noise reduction to any audiometry testing apparatus for the purpose of reducing ambient noise without affecting the hearing testing stimulus to provide reduced and accurate threshold measurements in the presence of ambient noise fields, and It is another object of this invention to provide a broadband reduction of ambient noise to be used to improve threshold testing when speech is used as the audiometry stimulus and to prevent the closed loop controller from modifying the test stimulus by use of a narrowband causal pre-filter, and It is yet another object of this invention to provide a new and unique psychoacoustic based design methodology for a narrowband feedback controller spanning the critical bandwidth and/or taking into account the masking patterns of normal human hearing thus maximizing the reduction and improving thresholds for pure tone audiometry, and It is a further object of this invention to introduce a switching controller design for pure tone audiometry where each tone has a different controller design thereby facilitating the maximization of the ambient noise reduction for each tone without compromising the stability margins of the feedback controller, and It is a still further object of this invention to provide a switching feedback controller that accomplishes similar objectives for one system under different circumstances such as changing disturbances or different desired time responses, wherein each controller has a similar design approach and are included in the feedback loop with an analog or digital switching mechanism, and Another object of this invention is to provide a psychoacoustic based active noise control approach implemented using a switching controller which selects different feedback noise control objectives thereby permitting the user to select the most desirable noise control behavior based on user preference and background disturbance, and Yet another object of this invention is to provide a switching controller that can be manually selectable by the end-user, incorporated into any feedback noise control device, where each controller controls different frequency bandwidths, and the switch permits the end user to select the most appropriate sounding controller specific to that end-user thereby providing, on an individual basis, the best sound quality available from any of the different designs, in the presence of (possibly) changing disturbances, and It is a final object of this invention to provide an automated means for switching between the different fixed gain controllers in an audiometry application, a sound quality application, or any other switching controller application, whereby the controller is selected based on quantitative measures of the disturbance or input variable such as sound pressure level, loudness, roughness, or some other desirable response which is plant and system dependent.

DETAILED DESCRIPTION AND PREFERRED EMBODIMENT

A detailed description of all of the intended structures and preferred embodiments for the switching feedback controller design is provided by reference to the figures included. These structures and embodiments will find unique applications in general fixed-gain feedback personal ANR systems for a variety of applications. The detailed descriptions presented next are intended for use in controlling ambient noise in audiometry testing environments. However, there are alternative intended embodiments that will be explained, in addition to the audiometry acoustic noise control applications.

Figure 1:
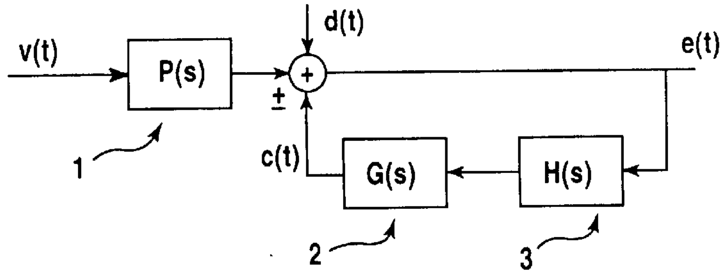
FIG. 1 illustrates a generalized feedback noise control block diagram designed for disturbance rejection.

The goal of disturbance rejection is a common one in many feedback control applications. FIG. 1 illustrates a generalized block diagram of a control architecture used to achieve this goal. The system to be controlled is represented by the plant transfer function G(s) (2). In general, this transfer function contains the dynamics of any system whose time response must be robust to non-desirable disturbances (represented by d(t)) and whose output must replicate an input or desired response represented by v(t). When the controller transfer function H(s) (3) is designed primarily to mitigate the effects of disturbances, the desired response can also be pre-filtered by P(s) (1) to ensure that the output e(t) follows the desired response v(t). In the past, ANR headsets have relied on similar control system architectures to provide suppression of the disturbance—in that case, the disturbance is the low frequency acoustic noise at the user's ear. This application is not concerned with a desired response. ANR communication headsets have been designed to reduce acoustic disturbances, as well as attempt to replicate voice signals that enter the control loop as a desired response. In both of these applications, the controller H(s) (3) is designed to reduce the frequency response of the closed loop transfer function to either known disturbances (allowing very specific design of H(s)) or uncertain disturbances (requiring a more general design for H(s)). The invention described below modifies this general architecture shown in FIG. 1 to introduce disturbance rejection in audiometry systems, leading to a unique implementation of active noise control. It will also be shown that the modifications are significant in their potential to improve the performance of a wider variety of active noise control applications, or even more general active control applications.

Figure 2:
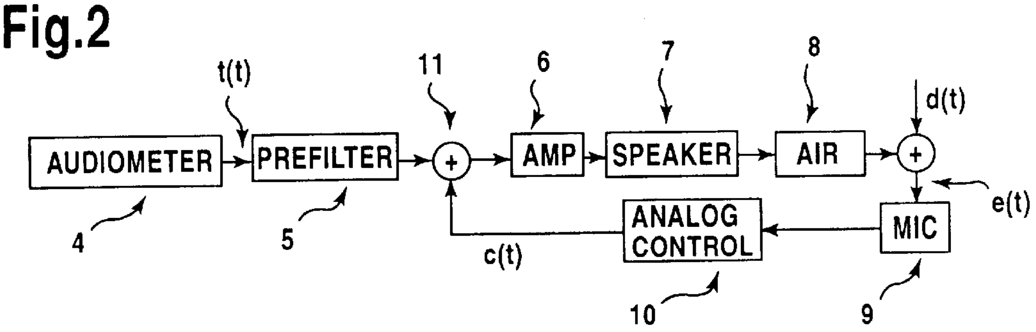
FIG. 2 shows a block diagram of the specific feedback controlled audiometry ANR system implemented with analog based hardware.

FIG. 2 illustrates a more specific representation of the disturbance rejection problem as applied to audiometry testing equipment. The desired response (at the test subject's ear) originates as a signal provided by conventional audiometers (4). This signal is usually either a pure tone or a speech signal; however, other test stimuli are used. (As will be seen, this feedback control invention is designed to incorporate any of these test stimuli t(t)). In order for disturbance rejection control to be performed, a disturbance sensor is required to transduce the acoustic noise to an electronic signal input to the controller. In the case of ambient noise control, the most appropriate sensor is a microphone (9) as illustrated in FIG. 2. The actuator that modifies the microphone sensor to reject the ambient noise is typically an electro-acoustic device such as a speaker (7). The speaker will also deliver the audiometry test signal, therefore a summing junction (11) is included prior to the speaker amplifier to add the disturbance suppression signal (i.e. the controller output c(t)) to the pre-filtered (5) audiometry test signal t(t). The plant (G(s) (2)) from FIG. 1 is now represented by the dynamics existing between the input to the amplifier (6) and the output of the error microphone (9). Included in these dynamics is the acoustic path between the speaker and the microphone represented in FIG. 2 by the "air" transfer function (8). For the purposes of these controller embodiments, it will be assumed that the dynamics between the speaker and microphone are not temporally changing, whether they are implemented in a headphone or otherwise.

Microphone (9) senses the same ambient pressure that the subject's eardrum receives, as long as the microphone is located within a certain distance of the ear canal; that distance depends on the desired frequencies to be controlled. The microphone placement is also a function of the zone-of-silence existing around an error microphone component in a personal ANR system and is not the object of this invention. Since the focus is on the controller implementation and design for audiometry, it will be hereafter assumed that the eardrum and the error microphone sense the same sound pressure level changes. (This is a valid assumption, especially at frequencies below 1000 Hz and close microphone location).

Applying disturbance rejection to audiometry, the goal is to reduce the ambient noise at the error microphone while passing the test stimulus through the system, unaffected by the noise reduction. To accomplish this goal, the controller design is done in the frequency domain by reducing the closed loop magnitude of the disturbance-to-error path across a range of frequencies. The mathematical realization of this controller is a transfer function that is a function of the Laplace variable "s". Any causal transfer function presented in terms of "s" can be physically realizable by building first and second order bi-quad operational amplifier circuits. This constitutes the analog hardware realization of the disturbance rejection problem for audiometry shown in FIG. 2 (10). The only hardware necessary to implement this noise control approach is the transfer function circuit built from analog electronics (10), the microphone amplifier (9), the speaker (current) amplifier (6), and a summing amplifier (11) to include the audiometer signal.

Figure 2A:
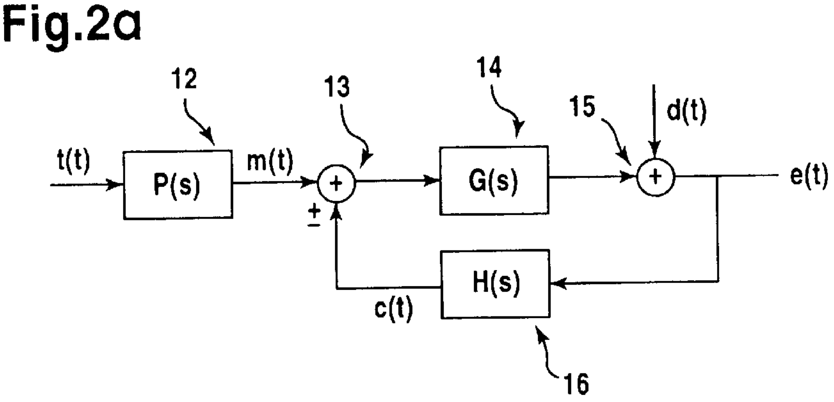
FIG. 2*a* illustrates the rearranged generalized feedback controlled disturbance rejection block diagram.

In order to provide the audiometer signal to the user unaffected by the closed loop controller, a prefilter (4) must be used to correct for the closed loop dynamics. Reconsider FIG. 2 in terms of FIG. 1. The plant (G(s) (2)) consists of the speaker amplifier, speaker, cavity and microphone. To simplify, FIG. 2*a* shows the plant (14), the controller (16), the test tone t(t), and the disturbance d(t) entering the loop in the proper locations (13)(15) for the audiometry disturbance rejection system. The equation below shows the contributions of both the test tone and the disturbance to the overall error signal:

$$e(t) \quad \frac{1}{(s)H(s)} d(t)$$

Ignoring the test signal momentarily, the disturbance-to-error path is minimized by increasing the gain of H(s) (16). (There are specific limitations on the gain/phase relationship of the open loop transfer function to prevent this system from becoming unstable, and are discussed momentarily). Now, ignoring the disturbance, the secondary control goal is to have e(t)=t(t) for all frequencies. In order for this to occur, the pre-filter P(s) (12) must satisfy the following equation:

In order for P(s) to be physically realizable over the entire bandwidth, the coefficient of t(t) in the error equation must be acausal (zero-pole excess) or have equal order numerator and denominator. This rarely occurs in practice. However, the test stimulus only extends over a finite bandwidth and therefore may be compensated as such with a causal filter. Within the bandwidth of the test stimulus, P(s) will appear as shown in the equation above. At higher frequencies, the filter can then be made causal by the inclusion of high frequency poles. This compensating filter can be created using analog electronics as described for the controller above.

Figure 3:
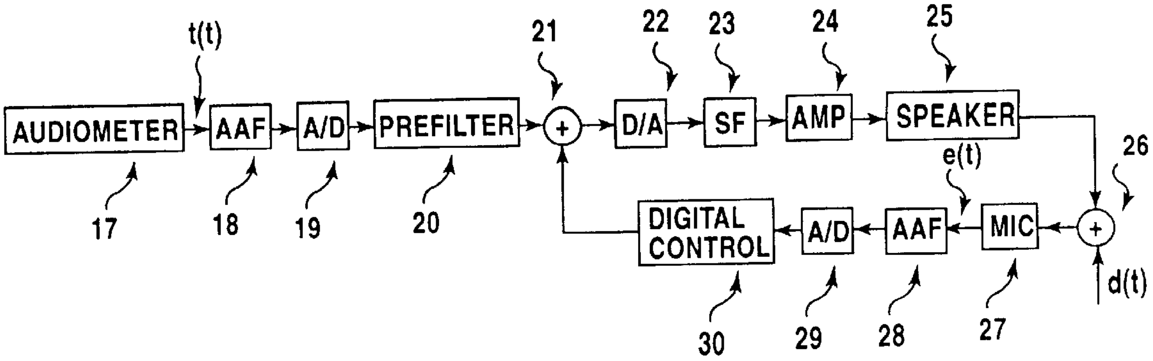
FIG. 3 shows a block diagram of the specific feedback controlled audiometry ANR system implemented with digital software and the required analog hardware.

An alternative implementation of the feedback controller and test stimulus compensator is presented in FIG. 3. The filter designs, both compensator (30) and pre-filter (20), can be implemented using a digital signal processor and digital based filter designs realized in the "z-plane". The test stimulus t(t) and error signal e(t) are first anti-alias filtered (18)(28) and sampled by the analog-to-digital converter (19)(29). They are then filtered with the fixed gain transfer functions (20)(30) designed for disturbance rejection (as the analog filters were) and sent out of the digital to analog converter (22). This output is then low pass filtered (smoothing filter (23)) to remove high frequency artifacts of the hold process and sent to the speaker amplifier (24). The plant is significantly changed by each of the additional pieces of hardware required for the sampled-data approach. The controller performance is likely to be somewhat limited by the inclusion of these additional dynamics, as they introduce significant linear phase roll-off. However, some performance can still be realized by an appropriate controller design process, described next.

Heretofore, the controller design itself has not been addressed because the process is identical for both analog and digital characterizations of disturbance rejection noise control for audiometry. Therefore, no specific reference to analog vs. digital is made during the following explanation. Based on the open loop dynamics (including the controller and all plant dynamics), the controller is designed by placing poles and zeros to maximize the open loop gain within the bandwidth of interest. The controller bandwidth is limited by both the design goal and the stability margins for feedback control. The design goal for audiometry is to reduce the noise in and around the bandwidth of the test signal. (This is addressed for individual test stimuli later). For feedback disturbance suppression, the open loop transfer function is to have greater than unity gain where the open loop phase is between 180 degrees and −180 degrees for negative feedback systems. For positive feedback, the open loop gain must be greater than unity between 0 and −360 degrees. For both negative and positive feedback, the open loop gain must be much less than unity when nearing these stability margins to avoid instabilities. Each of these margins can also occur at phase angles that are multiples of 360 degrees. For example, negative feedback disturbance rejection can have acceptable performance for a positive gain, open loop frequency response between open loop phase of 540 degrees and 180 degrees, 180 degrees and −180 degrees, −180 degrees and −540 degrees, etc. However, the magnitude of the open loop transfer function must be much less than unity when nearing these phase crossover frequencies or enerqy will be amplified in the closed loop system. This amplification is termed spillover.

Figure 4:
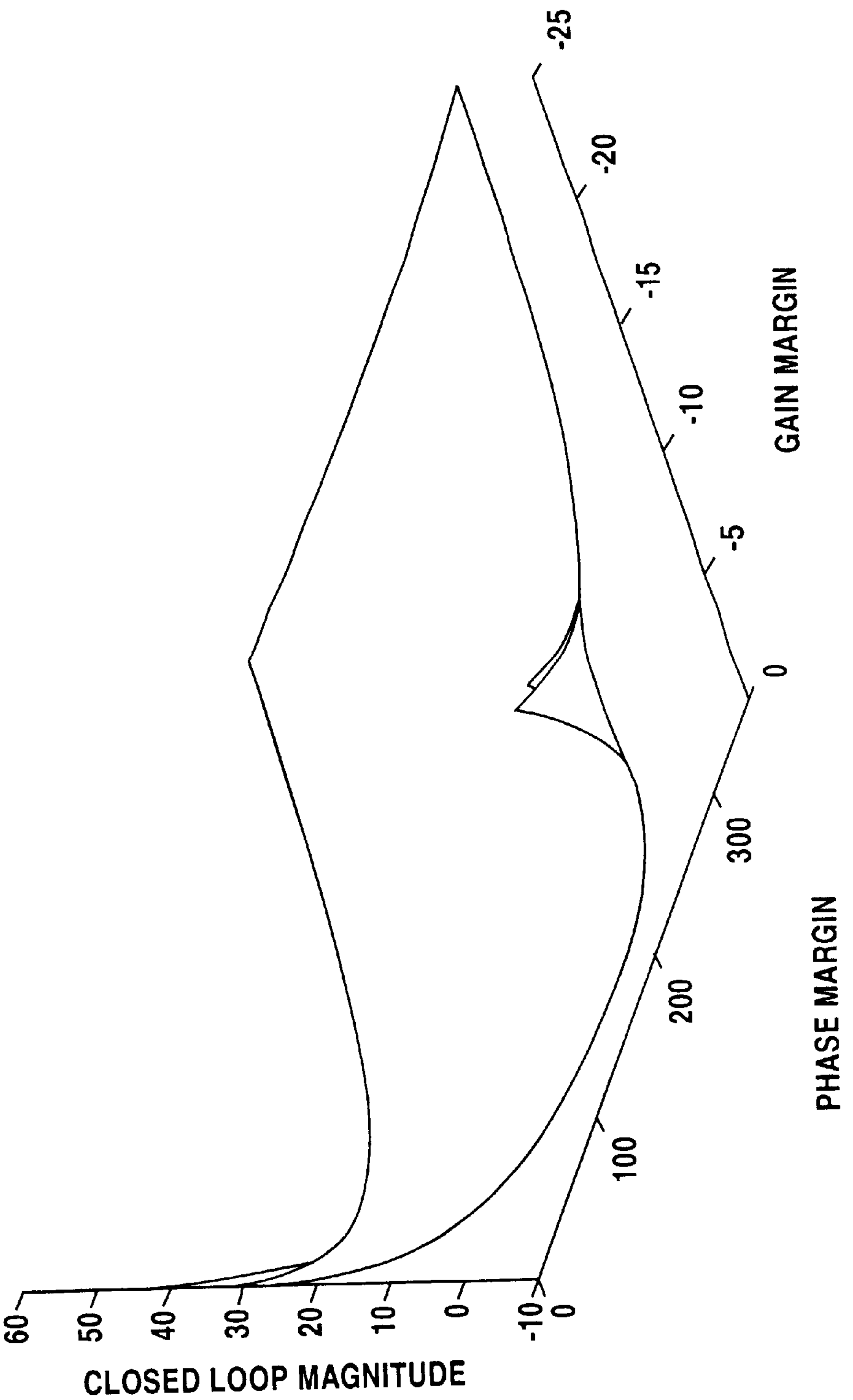
FIG. 4 illustrates a surface plot of closed loop spillover for varying positive gain margins and phase margins.

FIG. 4 shows the closed loop gain for various gain and phase margins. Because the goal is to reduce the level of the disturbance, it is essential that the controller design avoid adding energy to the closed loop system. To ensure this, the open loop gain must be less than −20 dB at the phase crossover points (where the open loop phase passes through a 360 degree multiple of 180 degrees for negative feedback). If however, the open loop gain is unity, the phase at this gain crossover point must be more than 30 degrees away from the nearest phase margin. When these criteria are not met, the user will perceive an amplification of the acoustic disturbance noise at the spillover frequencies. The presence of ambient disturbance noise during auditory testing can cause masking of the test stimulus and will adversely affect the test results. Therefore, these criteria are absolutely critical in the audiometry application since the user's environment must be very quiet. This aspect of disturbance rejection in audiometry testing must be adhered to in both analog and digital realizations of the feedback controller design. Less attention is paid to the spillover requirement when feedback noise control is applied to hearing protector headsets that operate in high noise environments. A higher closed loop gain near stability margins can be tolerated because the spillover is less noticeable to the user in those applications. However, too much spillover will affect the perceived performance of any personal ANR system.

The goal for disturbance rejection in audiometry systems is to improve the accuracy of hearing acuity measurements in higher noise environments than currently allowed by state-of-the-art passive noise reduction techniques. Existing feedback ANR headsets attempt to target as wide of a noise bandwidth as possible; although, they are typically designed to provide effectiveness up to only 1000 Hz. For the audiometry application, the fundamental objective is to reduce the perceived signal-to-noise ratio (SNR) of the test stimulus only. For speech stimuli, which spans frequencies from 200 Hz to 3–4 kHz, the design goal does not significantly deviate from that of hearing protectors. Therefore the design of the controller (when using speech as the test stimulus) will cover as wide a bandwidth as possible given the aforementioned stability constraints. The pre-filter mentioned above must also span the same bandwidth as the feedback controller to ensure unaffected delivery. For ANR, this bandwidth is not achievable because the zone of silence around the microphone will not be perceivable for frequencies much higher than 2 kHz because it is so small. Nevertheless, some improvement in threshold testing can occur by lowering the disturbance level in the low frequency region (0–2000 Hz) of the speech spectrum.

The ANR controller design is significantly different if the audiometer test stimulus is only a single tone. Several more innovations are discussed for use in pure tone audiometry, the most common of audiometry testing procedures. The bandwidth of ambient noise reduction required for threshold improvement of a pure tone stimulus is much less than that required for the speech stimulus. In fact, a novel design methodology is presented here that shows that this bandwidth of suppression is deterministic. First and foremost, the stability margins of the closed-loop system must be adhered to as described previously. Related to that constraint, the Bode integral gain theorom limits the overall magnitude change of the open loop transfer function (after the controller is in the loop) to avoid instabilities. This magnitude is proportional to the maximum amount of control, different for each situation, and must be evaluated on a case-by-case basis. A frequency domain, loop design process is now described, that will minimize the threshold shift perceived by the test subject for a given maximum limit of attenuation.

Figure 5:
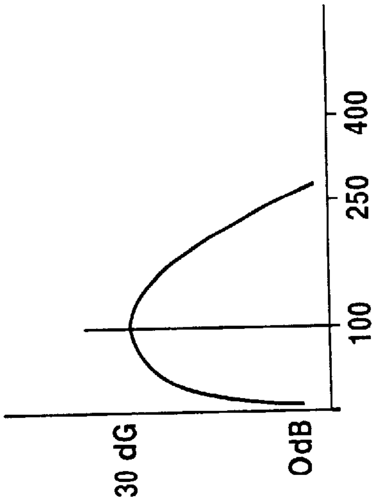
FIG. 5 illustrates an approximation of the 100 Hz center frequency masking pattern for normal hearing acuity at a relatively low ambient level.
Figure 5A:
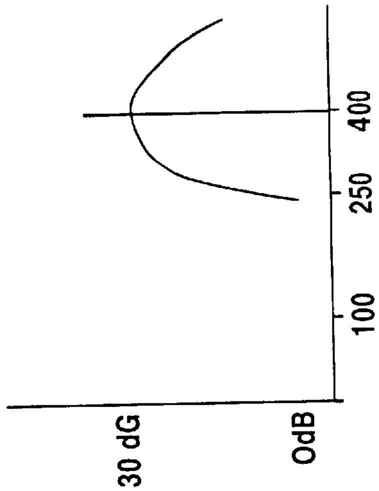
FIG. 5*a* illustrates an approximation of the 400 Hz center frequency masking pattern for normal hearing acuity at a relatively low ambient level.
Figure 5B:
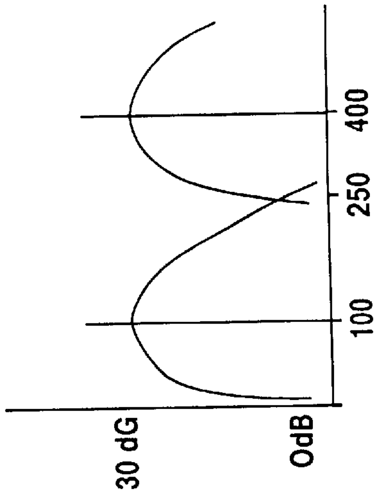
FIG. 5*b* illustrates both masking patterns from 5*a* and 5*b* plotted on the same graph.

An approximation of an auditory masking pattern associated with a 100 Hz tone is shown in FIG. 5 for a relatively low amplitude. Any other tone or narrowband noise with an amplitude and frequency that causes it to fall underneath this masking pattern, will not be perceivable to the subject with normal hearing acuity. This masking pattern shape, for the same amplitude levels, is generally the same for tones and narrowbands of energy at higher and lower frequencies, also. FIG. 5*a* shows an approximate masking pattern for a 400 Hz tonal at the same amplitude level. Suppose the audiometer test stimulus is a tonal at 250 Hz (a commonly used test tone in ANSI standard audiometry). Ambient noise existing below this test frequency can forward mask the test tone according to the general shape shown in FIG. 5. Although less imposing for higher amplitude disturbances, backward masking can also occur from frequency content above 250 Hz, as shown in FIG. 5*a*. (Note that the degree of forward and backward masking is a weak function of signal amplitudes, among other things). Now, if FIGS. 5 and 5*a* are overlapped as shown in FIG. 5*b*, and the amplitudes of both curves are adjusted up or down, shifting the center frequency of both high and low frequency masking patterns, a minimum point can be generated that lies directly on 250 Hz. The sound pressure level at this minimum point must correspond to the ambient SPL that is permissible to perform 0 dB HL hearing testing with subjects who have normal hearing. This is of course dependent on the ambient SPL and the maximum attenuation achievable by the feedback controller.

To determine both the shape and magnitude of the feedback controller used in pure tone audiometry, reconsider FIG. 5*b*. The magnitude difference between the highest SPL level and the lowest SPL level is approximately 30 dB. (This is a fabricated example to illustrate the design process). First, the highest permissible ambient noise level for 0 dB HL testing must be established in a controlled laboratory setting, using specific headphone plant and passive earcup performance. Suppose that level is 30 dB. Now, the masking patterns in FIGS. 5 and 5*a* can be amplified or reduced so that their intersection is at the frequency of interest (250 Hz) and maximum amplitude permissible by the passive measures (30 dB SPL). (Keep in mind that a simple amplification is not possible, and the masking patterns are tabulated based on human subject testing). Maintaining this intersection point, an iterative process of controller designs must begin. The maximum amplitude of attenuation required by the controller to prevent test tone masking, occurs at the intersection point (250 Hz) and the maximum amplitude for the given masking patterns is the difference in the maximum y-axis value of the masking pattern and the y-axis value at the intersection (30 dB in this example). A controller, which when incorporated with the plant, has a closed loop disturbance-to-error frequency response that matches the two masking patterns between the two highest peaks in FIG. 5*b* should be designed.

One of two events will occur: either a stable controller cannot be designed, or a stable controller can be designed. If the former occurs, the masking patterns must be reduced in magnitude and/or the center frequencies of the masking patterns must be moved closer to the intersection point (always deterministic based on passive performance and test stimulus frequency). The controller is then redesigned after the masking patterns are adjusted, to generate a stable controller. (Stability margins have been defined above). This process is repeated until the closed loop performance matches the masking pattern generated as in FIG. 5*b*. This design will also reveal the maximum ambient noise level in which audiometry can be performed using feedback disturbance rejection. Now, if the first design iteration produces a stable controller, the template masking patterns should be increased in amplitude and their center frequencies moved away from the test frequency to ensure performance in the highest ambient noise field allowable.

This iterative design process is complete when a stable controller has been designed having the closed loop shape of the overlapping masking patterns. Stability is defined specifically as shown in FIG. 4. There is in fact a gray area where the controller is neither performing well nor unstable. This usually manifests itself as "spillover", where the disturbance (ambient noise) is amplified instead of suppressed. This is usually considered problematic for personal ANR systems; however, the effect of spillover on the audiometry test tone signal is not nearly as critical. It is clear from the masking patterns presented in FIGS. 5, 5*a*, and 5*b* that spillover can be tolerated outside the bandwidth determined by the overlapping masking patterns, without affecting the threshold of the 250 Hz tone.

Therefore, adding noise outside the bandwidth is an acceptable design procedure in order to achieve higher levels of ambient noise attenuation near the test tone. This particular design alternative was not exercised for the 250 Hz controller example shown by FIGS. 6 and 7 in order to illustrate a completely stable controller.

Figure 6:
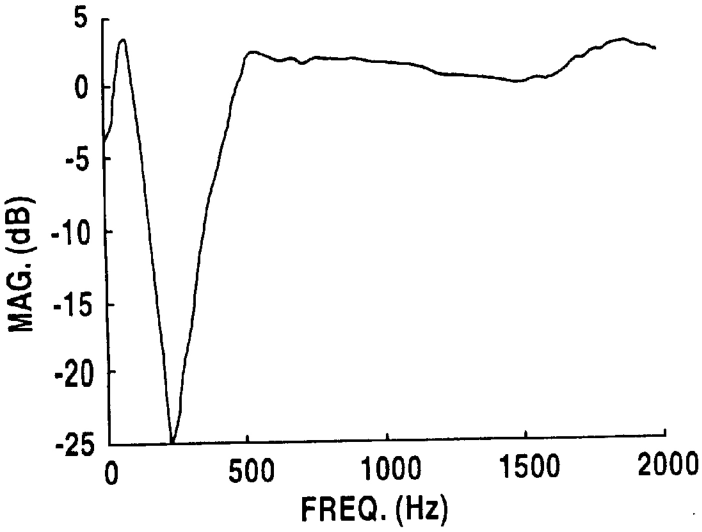
FIG. 6 is an example of the closed loop feedback controlled frequency response function from the disturbance to error path for a 250 Hz critical band controller design.
Figure 7:
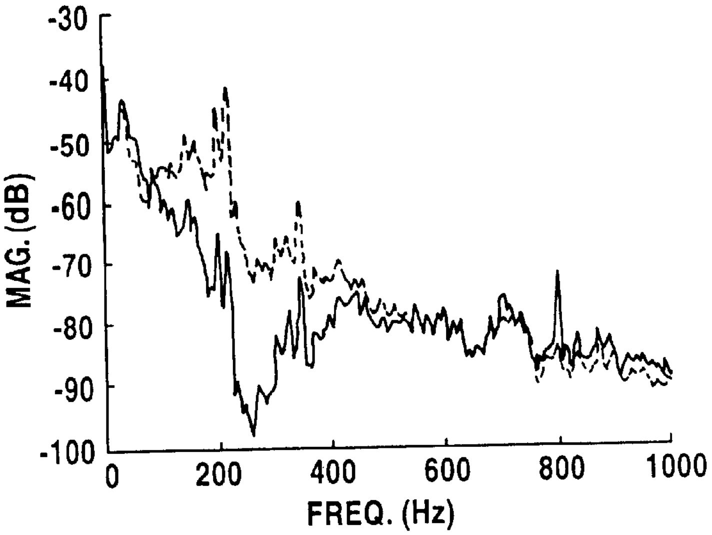
FIG. 7 shows the control performance for the critical band controller shown in FIG. 6. The controlled and uncontrolled error microphone SPL are plotted together.

FIG. 6 shows the closed loop disturbance-to-error frequency response using the design process described above for the 250 Hz test stimulus. FIG. 7 shows the controlled/uncontrolled error microphone signal. The transfer function of the controller incorporated an underdamped complex conjugate pole pair in order to elicit a high magnitude (open loop gain) over a relatively narrow (critical) bandwidth. Depending on the plant design, this may or may not be included as part of the design procedure. Forward masking of a higher frequency test tone only extends two critical bands above the frequency of the masking noise for very high amplitude disturbances and somewhat less for lower amplitude disturbances. So even though the controlled bandwidth shown in FIGS. 6 and 7 is slightly larger than a critical band, the feedback control approach introduced here is referred to as critical band control (this as opposed to the alternative terminology of masking pattern based control).

Figure 8:
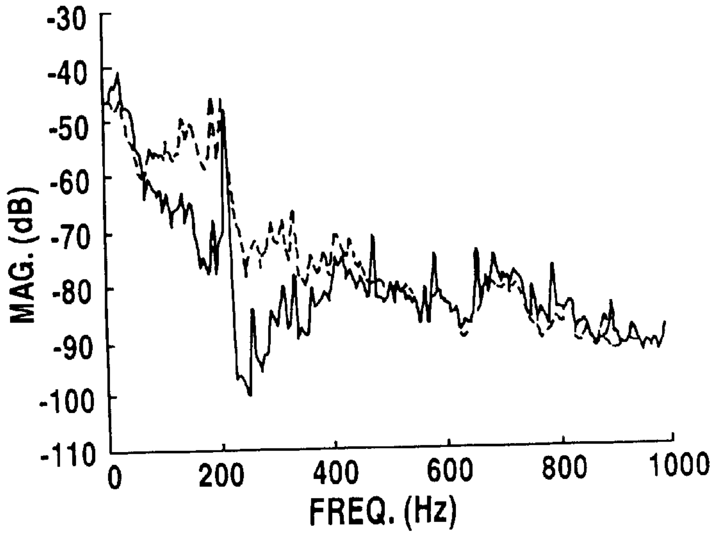
FIG. 8 shows a plot similar to FIG. 7, as applied to audiometry with the 250 Hz test tone being delivered to the subject. Both controlled and uncontrolled error microphone spectra are plotted together and each contain the 250 Hz test tone at the same level.

To complete the design of the pure tone ANR audiometer system using critical band control, the unaffected inclusion of the test stimulus must occur. This process, already described in detail for the speech stimulus audiometer, requires inverting the stimulus-to-error transfer function. It was emphasized that this can be accomplished (physically realizable) over the bandwidth of the stimulus signal only. This is also the case for pure tone audiometry but is much easier in this case. The bandwidth of the test stimulus is only a single frequency wide. Therefore the test stimulus needs only a simple magnitude adjustment (gain) in order to provide it to the error microphone unaffected by the closed loop controller. FIG. 8 illustrates the controlled/uncontrolled error microphone signal (as in FIG. 7) with the test tone included in both power spectra. It is clear that the test stimulus is at the same level with and without the controller engaged.

In order to show the improvements afforded by the critical band controller, pure tone audiometry tests at both 250 Hz and 500 Hz were performed on several subjects with the following results:

| | Test Tones in Quiet (56 dB) | | Test Tones in Pink Noise (60 dB) | |
|---|---|---|---|---|
| | 250 Hz | 500 Hz | 250 Hz | 500 Hz |
| Passive Only | 25 | 25 | 33 | 36 |
| ANR + Passive | 7 | 10 | 10 | 17 |
| Treshold Improvement | 18 | 15 | 23 | 19 |

The 500 Hz controller was designed using the same procedure as discussed above, for the 250 Hz controller. This procedure can be implemented for every test tone that provides useful attenuation and threshold improvement. In doing so, a new feedback controller implementation strategy is introduced which can be applied directly to pure tone ANR audiometery, to improving sound quality in ANC headsets, or any other feedback control application with changing system behavior.

Figure 9:
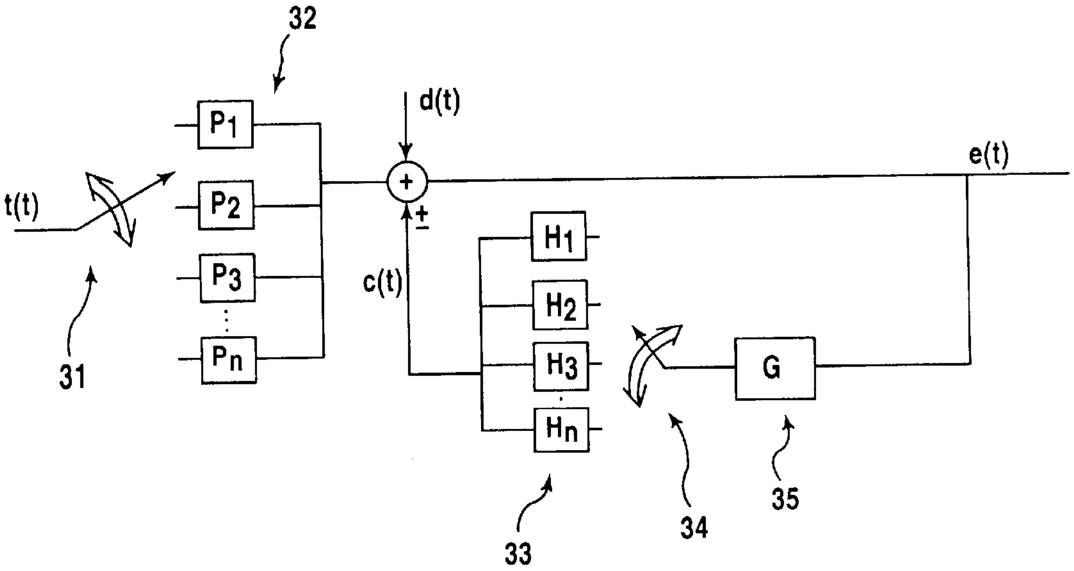
FIG. 9 illustrates the general concept of the switching controller implemented here, specifically for disturbance rejection. Depending on the control objective, the switching controller can be relocate in the closed (or open) loop.

Because of the stability limitation for gain and phase margins in feedback control, it is very difficult to implement more than one critical band controller simultaneously with another. However, for pure tone audiometry this is not necessary. Only one tone is tested at a time. When the subject's threshold of that tone stimulus is determined, the proctor switches to the next test tone. Taking advantage of this test procedure, a separate critical band controller can be designed and independently implemented for each test tone in order to maximize the threshold shift and disturbance rejection performance. Each controller is designed for one specific test frequency using the critical band controller design process described above. Thus, only one controller (the one designed for the specific test tone frequency) is implemented during the testing of each tone. This constitutes the switching controller innovation as applied to audiometry disturbance rejection. In addition to a separate controller for each test tone, a separate pre-filter is required to ensure that the desired signal is not adversely affected by the controller. FIG. 9 illustrates a general implementation of this concept as applied to disturbance rejection. The controller and/or pretilter can be implemented using either analog or digital hardware or software as mentioned above for the standard feedback controller for audiometry. The input (test stimulus, t(t)) is switched (31) between its own pre-filter ($P_1$, $P_2$, or $P_n$) (32) when that signal is under test. In addition, the controller ($H_1$, $H_2$, or $H_n$) (33) designed for that test tone is also connected (34) to close the loop on the disturbance rejection system. This method maximizes the noise control performance, and thus threshold improvement in noise, for each individual test tone. Various methods for implementing the switching process are also claimed, and will be described in detail.

Potential benefits realizable by the switching controller are not limited to the audiometry disturbance rejection application. The generalized switching controller application shown in FIG. 9 can be used in any feedback control system that has a design goal of disturbance rejection. Often, disturbances change with time and new controllers are required. Adaptive control is a technology that is used to account for these changes without designing new controllers. The fixed-gain switching controller (34) is an alternative to this approach that may be more cost effective and easier to implement. Control systems have other design goals in addition to disturbance rejection. The design goals for many systems are motivated by a desired time response (as opposed to a desired frequency response in the audiometry disturbance rejection application). Therefore the switching controller shown in FIG. 9 is illustrated for any general case as shown in FIG. 10 for any control system.

Figure 10:
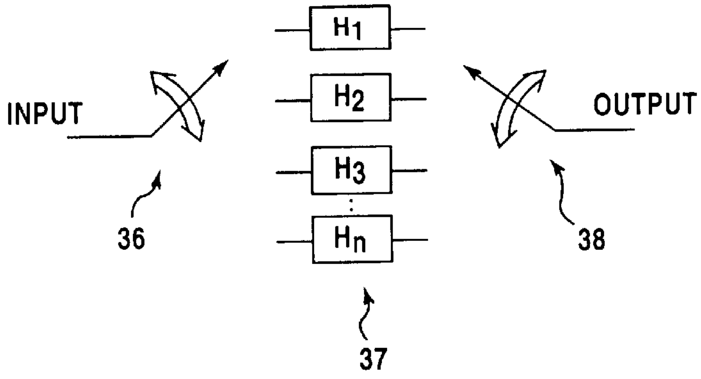
FIG. 10 illustrates the generalized switching controller which can be switched at the input or output or both. This structure can replace any feedback controller in the feedthrough or feedback path.

FIG. 10 illustrates the general switching controller which can be implemented in any control application. Every SISO feedback controller has an input and an output. FIGS. 1 and 2*a* illustrate two arrangements for feedback control where the plant is relocated in the physical loop. The controller (3) or (16) can also be relocated in the feedback loop to achieve different control goals. Wherever the SISO controller is placed in the loop, the switching controller shown in FIG. 10 can replace it in order to elicit different behaviors for a certain control goal (i.e. the switching controller is not limited to disturbance rejection in the feedback path as implied by the active noise control application). The controller and switch can also be implemented using analog hardware or digital software and/or hardware. This is why the controllers (33) and (37) are not shown as functions of "s" or "z", they can assume either realization. Both switches in FIG. 9 (36) and (38) are not necessary in most applications but both may be Included. Clearly both switches would have to simultaneously select the same controller (segment of (37)) in order for a signal path to exist from the input to the output. If either the input switch (36) or the output switch (38) is used to select the controller (37) (either supply the input to a single controller or detect the output of a single controller), the inputs or outputs of each controller can all be connected. This is shown as a special case for connected outputs in FIG. 9 following the prefilter (32) and controller (33). The switching procedure itself and which fixed gain controller is selected, is a function of the system requirements. These system requirements may be automatically determined based on quantitative data or they may be determined by the end user as in the application described next.

Active noise control headsets used for hearing protection and improved speech intelligibility in high noise environments are fairly common products in today's market. Those applications can be similar to the audiometry application, so that their design goal is also disturbance rejection of ambient noise. However, the ambient noise environment around the headset is usually changing, thus requiring a slightly different noise control to achieve either the greatest SPL reduction or the best improvement in perceived sound quality. The switching controller can provide just this feature to ANC applications. By designing a family of fixed-gain stable feedback controllers intended for ambient noise disturbance rejection, the most appealing (based on either qualitative or quantitative inputs) improvement in sound quality or noise reduction can be achieved. The controller designs themselves may all be based on disturbance rejection but the uniqueness among the different controllers can provide different characteristics to the end-user. One controller design may target a broadband reduction with a limited amount of rejection. Another may focus on reducing the SPL in one specific frequency bandwidth, affording a higher amount of attenuation. Many alternatives can be provided with such a device, and are intended to give the end-user a choice in selecting the most favorable improvement in sound quality for a variety of different noise fields or hearing mechanisms.

Each controller is separately included in the feedback control loop via a switch. To improve sound quality, this is a manual switch that effectively includes the human response in the control loop. The subject using the noise control can independently select the controller that improves the perceived sound the most. This will be based on the hearing acuity and personal preference of the end-user. These are qualities that are extremely difficult to quantify because they vary from user to user and from one noise environment to another. By allowing the user to select the desired performance, the designer can be assured that the ANC device can perform well in a variety of noise environments and will always meet the satisfaction of the end-user, within the available control options. For improving sound quality, the end-user is always the best judge.

Figure 11:
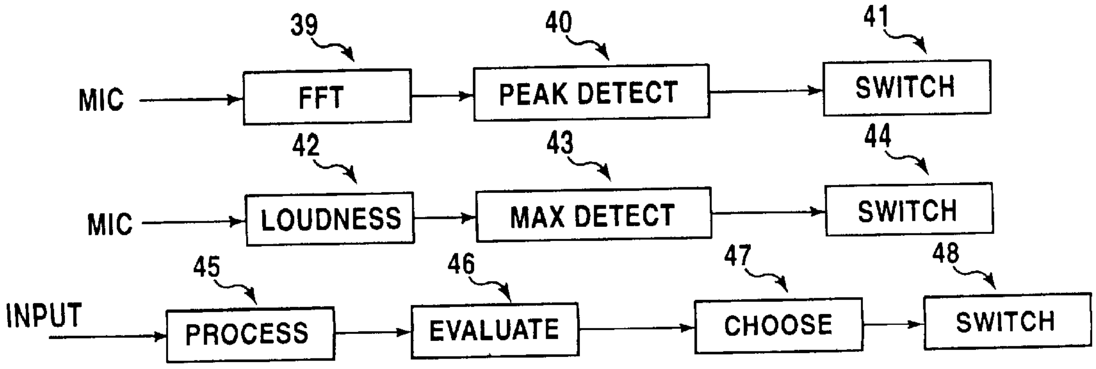
FIG. 11 illustrates a block diagram for implementing automatic switching between multiple controllers via either FFT analysis, sound quality analysis, or using any general decision making input.

For design goals that are different than improving sound quality, effective quantitative measures may be used to select the most appropriate controller for a given situation. For example, hearing protectors are intended to provide the user with the highest level of ambient noise reduction, often based on A-weighted SPL. In this situation, an automated selection device can be implemented to switch between different fixed gain controllers to most effectively reduce the overall A-weighted SPL. The first diagram in FIG. 11 illustrates one possible implementation for this type of device. A microphone and signal processing device can calculate the ambient A-weighted SPL (39) and determine the frequency bandwidth containing the most energy (40). Using a simple algorithm connected to an automated switch (41), the pre-designed fixed gain controller that most effectively targets that bandwidth can be automatically selected. This is extremely advantageous when the ambient sound field changes SPL shape over time and a new disturbance needs to be controlled. Current fixed-gain controller, personal ANR system technology does not permit different control efforts for different disturbances because only one controller is included in the product.

This particular automatic switching approach finds specific utility in the pure tone audiometer. If the switch is not incorporated into the audiometer, the switching algorithm can be implemented to automatically select the appropriate critical band controller. Each test tone is provided to the critical band switching controller separate from the error microphone signal. This signal can be used to switch both the pre-filter and the controller automatically. For example, the test tone at 250 Hz can be identified as such via an FFT operation (39) peak detection algorithm (40). Once the signal has been identified as 250 Hz, a microcontroller-based switch (41) can connect the test input to the 250 Hz pre-filter and the plant output to the 250 Hz critical band controller, respectively. As soon as the signal changes, the FFT peak will follow the switch. The switching algorithm itself can be implemented with a DSP sampling the input (test stimulus from the audiometer) or with a vast array of analog electronics including a frequency peak detector controlling transistors to drive the switch to different pre-filter's and/or controllers.

The automated switching procedure (either analog or digital) can be useful in any implementation of the switching controller. Besides the audio meter application, improvement of sound quality in ANC devices can also benefit from an automated switching controller. Clearly, the manual switch will provide the best improvement in sound quality for any user, but the responsibility may be undesirable to the user. In such a case, sound quality metrics intended to quantify human perception of sound can be used. A microphone (either the error microphone or a separate uncontrollable sound field measurement) signal is used to generate measures of loudness, roughness, amplitude variations, or any other measurable quality of sound (42). This data is then analyzed (43) and used to select the controller that will ameliorate the disturbance(s) most effectively (44). If amplitude variations are a primary concern, a controller that targets the bandwidth where these variations are most significant can be selected based on that signal. This concept is illustrated as the second automated switching option in FIG. 11. The end result will be to provide the user with the best sound quality improvement as determined by the chosen quantitative metric.

To further generalize and conclude the explanation of the automated switching controller, consider the third option illustrated in FIG. 11. For any switching controller, a physical measure that relates to the control goal exists or can be derived (termed "input"). This measure can then be used to make a decision to select the most appropriate controller for the given task. The input is evaluated (45)(46) and a decision is made (47) that governs the choice of controller. The choice of the input signal is important and depends on each specific situation, as do the rules for controller selection.

Several innovative aspects of the present invention have been presented throughout the preceeding discussion. First, feedback noise control disturbance rejection for specific application to audiometry and hearing testing apparatus was described with special attention being given to delivering the audiometry test stimulus without alteration, via the pre-filter. In addition, speech stimulus audiometry requires a complex pre-filter to ensure proper delivery to the test subject. Specific implementation of the general disturbance rejection audiometer was presented using both analog and digital feedback control implementations. Secondly, the critical band controller was discussed as part of this invention. The invention relies on the auditory physiological features to achieve narrowband disturbance rejection for pure tone audiometry. The masking patterns of normal human hearing were used to generate a feedback controller frequency response that provides the highest threshold shift available for pure tone active noise control audiometry. Since each test tone was evaluated separately, the maximum noise reduction for each individual test tone was achieved by implementing the switching controller for pure tone ANR audiometry. The switching controller design itself, however, is not limited to audiometry or disturbance rejection applications. Any implementation of a feedback controller presented with varying inputs can benefit from this technology. One specific instance presented was active noise control headsets. The manual switch for this application promises to drastically improve sound quality for ANC headset users. Finally, automatic switching between fixed-gain feedback controllers was presented. Specific examples were provided to explain the general concept that must be evaluated and designed separately for each switching controller implementation.

Having described the invention in both general and specific terms, it will be obvious to those of ordinary skill in the art to make various changes to the configuration and operating system without departing from the scope of the appended claims.

What is claimed is:

1. A method for reducing ambient noise in hearing testing environments without corrupting a hearing test stimulus signal, said method involving multiple switching controllers each employing a feedback control including employing a system having the following characteristics, sensing means for sensing either the ambient noise or both the ambient noise and test stimulus, a feedback control design approach incorporating multiple controller designs, comprising;

multiple first control means for generating a control signal, actuation means for delivering the control signal, multiple pre-filtering means for separately modifying the test stimulus to offset the attenuation from said first control means when provided to said actuation means, utilizing the system to reduce the ambient noise perceived by a test subject without affecting the test stimulus to thereby deliver accurate hearing test results.

2. The method as described in claim 1 wherein said sensing means is a microphone.

3. The method as described in claim 1 wherein said control means is a filter utilizing analog electronics, placed in either the feedthrough path or the feedback path of the control loop, utilizing either negative or positive feedback control, and being configured such that when the loop is closed around the entire system, some undesirable frequency content in the environment is attenuated at and around the said sensing means.

4. The method as described in claim 3 wherein said pre-filtering means has a frequency response that is the inverse of the closed loop plant over the bandwidth of the test signal so as to produce a physically realizable causal filter but also properly shaping the test stimulus to arrive at the test subject unaffected by the control loop.

5. The method as described in claim 4 wherein said inverse constitutes a gain only at a single frequency when test stimuli are single frequency tones.

6. The method as described in claim 4 wherein said inverse covers the bandwidth of the test stimulus and then incorporates additional poles to give the filter a causal response.

7. The method as described in claim 1 wherein said second control means is implemented using either analog hardware or digital hardware and/or software.

8. The method as described in claim 1 wherein said first control means is a filter designed using digital based softare and/or hardware.

9. The method as described in claim 1 wherein said actuation means is a speaker or headphone speaker.

10. The method as described in claim 9 wherein said actuation means delivers both the test stimulus and the controlling output simultaneously which is added prior to delivery to said actuation means.

11. A feedback control system incorporating multiple controllers for use in active noise control comprising multiple switching controllers each accompanied by seperate pre-filtering means a means for switching between each controller that disconnects all other controllers from the system, an actuation means for affecting the system in a manner prescribed by the controller means, a sensing means for providing an input to said selected controller means, whereby each of the said multiple controllers accomplishes a similar or different control goal for different loop inputs at different points in time determined by said switching means.

12. The system as described in claim 11 wherein the controller may be negative feedback or positive feedback in order to maximize control performance and that switching between the two for a given controller design can be effected.

13. The system as described in claim 10 wherein the said controller contains analog hardware.

14. The system as described in claim 10 wherein the said controller contains digital hardware or software.

15. The system as described in claim 10 wherein the said set of controllers are designed for the active noise control of certain different frequencies and bandwidths which may or may not periodically change depending on the ambient noise field and desired performance.

16. The system as described in claim 10 and including an automatic feature to said switching means for selectively and automatically switching between one controller and another, wherein the said switching between controllers is automatically done by said feature using a microprocessor or non-human controlled switch by analyzing the sound field via a fast fourier transform operation, appropriate frequency weighting, and selecting the controller which will have the greatest reduction in sound pressure level or FFT magnitude.

17. The system as described in claim 10 wherein the said switching means is a microprocessor, and said switching is automatically done using said microprocessor by analyzing the sound field via any psychoacoustic metric intended to quantify human hearing qualities.

18. The system as described in claim 16 wherein the said switching between controllers is automatically done using a microprocessor or non-human controlled switch by using some input from the physical system to analyze a rule or set of rules used to determine the best fixed gain controller to implement for a given input or type of input that then elicits the appropriate switching response to engage the chosen controller.

19. The approach as described in claim 10 wherein the said switching between controllers is manually performed by the end user in order find the best of the available controllers to maximize the sound quality or reduction in the perceived ambient noise level or if used in other non-ANC situations, to elicit the most user desirable response.

20. An active noise control system to be used in pure tone audiometry testing incorporating multiple feedback controllers attenuating ambient noise, said system comprising multiple switching controllers each accompanied by separate pre-filtering means a switching means to select different controllers associated with different test tones, a means to configure each separate controller so that the maximum threshold shift occurs for the frequency of the test tone that the controller is associated with, a means for separately modifying each test tone to conform to a standardized calibration procedure, whereby said noise control system is totally adaptable to all situations encountered in pure tone audiometry testing.

21. The system as described in claim 20 wherein said controller or controllers has as its primary dynamic or dynamics an underdamped complex conjugate pole pair with its natural frequency the same as the frequency where the maximum control effectiveness is desired being introduced into the open loop system via the controller design or naturally or unnaturally occuring in the system upon which control is to be excercised.

22. The system as described in claim 20 wherein said controller or controllers are designed to have a bandwidth similar to the critical bands of a human with normal hearing acuity with the amplitude being limited by the stability of the controller and the center frequency corresponding to each test stimulus.

23. The system as described in claim 20 wherein said controller is designed to have a disturbance rejection region that acts as an inverse filter whose shape is based on the forward and reverse masking psychoacoutic phenomena observed for human auditory systems.

24. The system as described in claim 20 and including audiometer hardware wherein said switch is not directly coupled to the audiometer hardware and is controlled by a manual switch operated by the user.

25. The system as described in claim 20 wherein said switch is included in the audiometer hardware and is controlled by the same switch as the test tone, thereby automatically selecting the appropriate controller when the test tone is selected.

26. The system as described in claim 20 wherein said switch is not manually adjustable and is performed by a selection procedure based on the current test tone frequency incorporating analog or digital hardware or software to select the controller corresponding to the current test tone.

27. A method for reducing ambient noise in hearing testing environments without corrupting a hearing test stimulus signal, said method involving a switching controller employing feedback control including employing a system having the following characteristics, a sensing means for sensing either the ambient noise or the ambient noise and test stimulus, a feedback control design approach incorporating multiple controller designs comprising a first control means for generating a control signal, an actuation means for delivering the control signal, a second control means for separately modifying the test stimulus to leave it unaffected when provided to said actuation means, said second control means has a frequency response that is the inverse of the closed loop plant over the bandwidth of the test signal so as to produce a physically realizable causal filter but also properly shaping the test stimulus to arrive at the test subject unaffected by the control loop and where the inverse covers the bandwidth of the test stimulus and then incorporates additional poles to give a filter a causal response, utilizing the system to reduce the ambient noise perceived by a test subject affecting the test stimulus to thereby deliver accurate audiogram.

28. An active noise control system to be used in pure tone audiometry testing incorporating multiple feedback controllers attenuating ambient noise, said system comprising a switching means to select different controllers associated with different test tones, a means to configure each separate controller so that the maximum threshold shift occurs for the frequency of the test tone that the controller is associated with, a means for separately modifying each test tone to conform to a standardized calibration procedure, said controller or controllers has as its primary dynamic or dynamics an underdamped complex conjugate pole pair with its natural frequency the same as the frequency where the maximum control effectiveness is desired being introduced into the open loop system via the controller design or naturally or unnaturally occurring in the system upon which control is to be exercised, whereby said noise control system is totally adaptable to all situations encountered in pure tone audiometry testing.

29. A system as in claim 28 wherein said controller or controllers are designed to have a bandwidth similar to the critical bands of a human with normal hearing acuity with the amplitude being limited by the stability of the controller and the center frequency corresponding to each test stimulus.

30. A system as in claim 28 wherein said controller is designed to have a disturbance rejection region that acts as an inverse filter whose shape is based on the forward and reverse masking psychoacoustic phenomena observed for human auditory systems.

31. A system as in claim 28 wherein said switch is included in the audiometer hardware and is controlled by the same switch as the test tone, thereby automatically selecting the appropriate controller when the test tone is selected.

* * * * *

UNITED STATES PATENT AND TRADEMARK OFFICE

CERTIFICATE OF CORRECTION

| | | |
|---|---|---|
| PATENT NO. | : 6,160,893 | Page 1 of 1 |
| APPLICATION NO. | : 09/123974 | |
| DATED | : December 12, 2000 | |
| INVENTOR(S) | : William Richard Saunders and Michael Allen Vaudrey | |

It is certified that error appears in the above-identified patent and that said Letters Patent is hereby corrected as shown below:

Column 1, line 4, insert the following section title and paragraph:

--GOVERNMENT RIGHTS

This invention was made with Government support under contract F41624-97-C-2005 awarded by the Department of the Air Force. The Government has certain rights in this invention. The U.S. Government has a paid-up license in this invention and the right in limited circumstances to require the patent owner to license others on reasonable terms as provided by the terms of contract F41624-97-C-2005 awarded by the Department of the Air Force.--

Signed and Sealed this

First Day of December, 2009

David J. Kappos

David J. Kappos
*Director of the United States Patent and Trademark Office*